United States Patent
Braeuninger-Weimer et al.

(10) Patent No.: US 6,488,183 B1
(45) Date of Patent: Dec. 3, 2002

(54) FLEXIBLE URGING MECHANISM AND DISPENSING KIT INCORPORATING SAME

(75) Inventors: Willmar Braeuninger-Weimer, Rastatt (DE); Arnold Neuhold, Farchant (DE)

(73) Assignees: Weimer Pharma GmbH (DE); L+N Plast Vertriebs GmnH (DE)

( * ) Notice: Subject to any disclaimer, the term of this patent is extended or adjusted under 35 U.S.C. 154(b) by 0 days.

(21) Appl. No.: 09/857,058

(22) PCT Filed: Nov. 26, 1999

(86) PCT No.: PCT/EP99/09198

§ 371 (c)(1),
(2), (4) Date: May 31, 2001

(87) PCT Pub. No.: WO00/32496

PCT Pub. Date: Jun. 8, 2000

(30) Foreign Application Priority Data

Dec. 3, 1998 (DE) .......................... 198 55 764

(51) Int. Cl.[7] .............................................. G01F 11/06
(52) U.S. Cl. ...................................... 222/326; 222/494
(58) Field of Search .......................... 222/83, 326, 327, 222/494

(56) References Cited

U.S. PATENT DOCUMENTS

| | | | |
|---|---|---|---|
| 4,318,499 A | | 3/1982 | Hamilton |
| 4,356,938 A | * | 11/1982 | Kayser ..................... 222/327 |
| 5,062,551 A | | 11/1991 | Goldstein et al. |
| 5,207,659 A | * | 5/1993 | Pennaneac'h et al. ....... 222/494 |
| 5,511,699 A | * | 4/1996 | Tepic ......................... 222/326 |
| 5,782,633 A | * | 7/1998 | Muhlbauer ................. 222/326 |
| 6,241,412 B1 | * | 6/2001 | Spies et al. ................. 222/83 |
| 6,293,431 B1 | * | 9/2001 | Seymour et al. ............ 222/83 |

FOREIGN PATENT DOCUMENTS

EP  0 051 994 A  5/1982

* cited by examiner

Primary Examiner—Joseph A. Kaufman
(74) Attorney, Agent, or Firm—Miles & Stockbridge P.C.; Edward J. Kondracki; John C. Kerins

(57) ABSTRACT

An urging device includes: an urging actuator (7); and an urging mechanism actuatable by the urging actuator in an urging direction for effecting a translational movement of a member (3), the urging mechanism being configured such that, upon actuation thereof, at least a first portion (11a) thereof moves in a first direction, and a second portion thereof moves in a second direction different from the first direction, and a second portion thereof moves in a second direction different from the first direction. Additionally, a dispensing kit (5) implements the above urging device. The dispensing kit comprise a dispensing cartridge (15) which includes a cartridge body. A cartridge actuator (21) is disposed at the head portion of the cartridge body. The kit further includes a dispensing device having a dispensing device body (5) for receiving the cartridge body therein and defining an opening at one end thereof such that, when the cartridge body (17) is within the dispensing device body, the opening of the dispensing body (57) is in registration with the opening of the cartridge body. A dispensing actuator is disposed at another end of the dispensing device body, and the above-described urging mechanism is disposed in the dispensing device body for being actuatable by the dispensing actuator to urge the cartridge actuator in the dispensing direction when the cartridge body is received within the dispensing device for effecting a dispensing of a content of the cartridge body therefrom.

17 Claims, 4 Drawing Sheets

FLEXIBLE URGING MECHANISM AND DISPENSING KIT INCORPORATING SAME

CROSS REFERENCE TO RELATED APPLICATIONS

The instant application claims priority to application number DE 19855764.7, filed in Germany on Dec. 3, 1998, the contents of which are incorporated herein by reference.

FIELD OF THE INVENTION

The instant invention relates to an urging device for transferring force in a linear fashion, the urging device including an urging mechanism having intermeshing parts for transferring this force. The invention further relates to dispensing kits have a reservoir body and incorporating the urging device for effecting a dispensing of a content of the reservoir body. The content may be solid in the form of tablets or capsules, or fluid, such as a liquid or paste, and is adapted to be pushed out of the reservoir body by a plunger subjected to translation controlled by the user and moving within the reservoir body.

BACKGROUND OF THE INVENTION

Urging devices of the above type are known for example from U.S. Pat. No. 5,765,320, which discloses a linear actuator as a drum 4, a stiff flexible ribbon 1 wound on the drum, a device for rotating the drum at least to partially unwind the ribbon thereon, a guide funnel 5 for gradually forming the ribbon into a tubular configuration, and an attachment device 11 at a free end of the ribbon for connection to an object to be moved in a linear path. The actuator thus converts rotary motion to linear motion.

Additionally, German laid open patent application, DE 2162938 discloses a thrust and traction element of variable length made of two spoolable parts wound about two rotatable drums 3 and 4 respectively. Each spoolable part includes a number of protrusions and corresponding recesses for intermeshingly and formfittingly receiving the other spoolable part upon being wound by the drums 3 and 4, as shown in FIGS. 1 and 4. Each spoolable element further includes a toothed portion at one face thereof adapted to be driven by a correspondingly toothed rotatable gear member 15. The intermeshing of the two spoolable parts results in the formation of a rigid member or rod.

Urging devices of the prior art have as a disadvantage that they make inefficient use of space, requiring either a single bulky region for housing a portion of the urging device, as in U.S. Pat. No. 5,765,320, or requiring complex, multi-parts and cooperating mechanisms, as disclosed in DE 2162938.

Additionally, dispensers of the above type are used for holding and dispensing dosed amounts of fluids, or even for holding and dispensing tablets or capsules. In some instances, the volume to be dispensed or dosed is in the range of milliliters. Dropper bottles such as these may also be used for the purpose of dispensing oral or topical applications, where, if a fluid is involved, the fluid is dispensed drop-wise according to a predetermined prescription.

U.S. Pat. No. 5,330,721 discloses a step pipette having a dosing rack 5 and therein a dosing toothing 14, a strike S meshing with the dosing toothing, a filling rack 13 connected with the dosing rack by a gear 16, a striker spring 12 as well as a release member for releasing the tension of the striker spring after the last full-length stroke. The solution according to this patent ensures that the last liquid dose is dispensed from the pipette.

U.S. Pat. No. 4,954,000 discloses a dispenser of a compact product 3 contained in a cylindrical reservoir 1. The product is ejected via a plunger 4 that is displaceable in translation in the reservoir and is mounted at the end of a threaded rod 5 which cooperates with a nut 9. The rod is driven in rotation incrementally via a pushbutton 8. The support 7 of the mechanism and of the nut is movable with respect to the reservoir by means of a thread. The nut which cooperates with the rod 5 is slit along a diametrical plane, to allow the re-pressing of the rod when the half nuts are capable of spreading apart. The reservoir includes a frusto-conical surface, which assures the pinching of the half-screws when the mechanism is put into place at the base of the full reservoir.

Dispensers of the prior art disadvantageously use urging mechanisms which extend along a length of the reservoir the content of which is to be dispensed, thus making inefficient use of space, especially where the dispenser is to be used as a lifestyle article apt to be carried in one's pocket or handbag, such as, for example, a liquid drop dispenser for drops to be taken regularly during the day. Were the dispensers of the prior art to be used, they would be impractically long, complicating transport for the user. Additionally, in order to effect dosing of the content of the reservoir body, these dispensers typically involve complicated mechanisms. Moreover, the delivery mechanisms in dispensers of the prior art often result in the fluid content of the dispensers dripping, especially after delivery, thus causing unnecessary waste and possible soiling of the means carrying the dispenser.

SUMMARY OF THE INVENTION

It is an object of the invention to provide a simplified urging device for transferring force in a linear fashion which provides a space saving alternative to urging devices of the prior art. It is a further object of the invention to provide an dispensing kit using the urging device according to the invention, the kit being compact in its longitudinal direction with respect to dispensers of the prior art, thereby allowing easy transport and handling.

The above objects, and other objects to become apparent as the description progresses, are fulfilled by providing an urging device comprising: an urging actuator; and an urging mechanism disposed to be actuatable by the urging actuator in an urging direction for effecting a translational movement of a member to be moved in the urging direction, the urging mechanism being configured such that, upon actuation thereof by the urging actuator, at least a first portion thereof moves in a first direction, and a second portion thereof moves in a second direction that is different from the first direction.

According to one embodiment of the invention, the urging mechanism comprises a flexible portion forming the first portion and the second portion upon actuation of the urging mechanism, the urging device further including a transition mechanism coupled to the flexible portion for guiding a direction change of the flexible portion from the first direction to the second direction. The transition mechanism may comprise the urging actuator.

According to another embodiment of the invention, the flexible portion is a first flexible portion and the transition mechanism is a first transition mechanism, the urging mechanism further comprising a second flexible portion and a second transition mechanism coupled to the second flexible portion for guiding a direction change of the flexible portion from the first direction to the second direction, the first flexible portion and the second flexible portion being adapted to engage one another at an engaging zone after having been guided by the first transition mechanism and the second transition mechanism thereby forming a consolidated longitudinal member corresponding to the second portion of each of the first flexible portion and the second flexible portion, the consolidated longitudinal member being effective for effecting the translational movement of the member to be moved in the urging direction.

According to a further embodiment of the invention, the first flexible portion and second flexible portion are configured to engage one another at the engaging zone by friction.

According to yet another embodiment of the invention, each of the first flexible portion and second flexible portion has teeth disposed thereon which respectively engage one another at the engaging zone for forming a rigid member or rod corresponding to the consolidated longitudinal member.

Advantageously, the second direction may differ from the first direction by an angle of 180 degrees, and the urging device may further include a first biased member connected to the first transition mechanism and a second biased member connected to the second transition mechanism, the first biased member and the second biased member being respectively effective for biasing the first transition mechanism and the second transition mechanism in the first direction, such that, upon an actuation of the urging actuator, the first biasing member and the second biasing member are compressed for respectively allowing the first transition mechanism and the second transition mechanism to move in the second direction, and that, upon a release of the urging actuator, the first transition mechanism and the second transition mechanism move in the first direction thereby effecting an engagement of the first flexible portion and the second flexible portion with one another without actuation by the urging actuator.

According to one embodiment of the invention, the urging actuator comprises a rod biased in a direction opposite the urging direction, the teeth on each of the first flexible portion and the second flexible portion further comprising repeated sets of shaped teeth, each set including a plurality of grooved teeth and a solid tooth such that, upon, actuation of the urging actuator, the rod presses upon the solid tooth of a nearest flexible portion for intermeshing the teeth with one another in the urging direction, and further such that, upon release of the urging actuator, the rod is biased in a direction opposite the urging direction through the grooved teeth, the biasing members connected to the transition mechanisms thereafter being effective for causing a further intermeshing of the teeth for further engagement of a solid tooth by the rod.

According to one aspect of the invention, the urging device may further include a microprocessor coupled to the urging actuator for controlling an actuation thereof thereby effecting a controlled movement of the member to be moved in the urging direction.

The object of the invention, and other objects to become apparent as the description progresses, is further fulfilled by providing a dispensing kit comprising a dispensing cartridge which includes a cartridge body defining an opening at one end thereof and a head portion at another end thereof. A cartridge actuator is disposed at the head portion. The kit further includes a dispensing device having a dispensing device body for receiving the cartridge body therein and defining an opening at one end thereof such that, when the cartridge body is within the dispensing device body, the opening of the dispensing device body is in registration with the opening of the cartridge body. A dispensing actuator, such as, for example, a biased button, is disposed at another end of the dispensing device body, and an urging mechanism is disposed in the dispensing device body for being actuatable by the dispensing actuator to urge the cartridge actuator in a dispensing direction when the cartridge body is received within the dispensing device for effecting a dispensing of a content of the cartridge body therefrom, the urging mechanism being configured such that, upon actuation thereof by the dispensing actuator, at least a first portion thereof moves in a first direction and a second portion thereof moves in a second direction that is different from the first direction The content of the cartridge body may either be made of a fluid or a solid, that is, a plurality of solid parts such as tablets or capsules, including gel capsules. The dispensing kit according to the invention is especially suited for the delivery of pharmaceuticals, foodstuff including herbs, herbal preparations, vitamins and minerals and cosmetics, thereby being advantageously useful as a lifestyle article which may be conveniently carried in one's pocket or handbag, and conveniently handled. The volume to be filled in such cases is generally in the range of milliliters. The dispensing device and cartridge assembly according to the invention allows simplified handling by allowing a direct oral or topical administration. Advantageously, the content of the cartridge may be applied as a medium to be mixed after it is dispensed with dissolving or carrier media or with another substance for creating a further preparation.

According to one aspect of the invention, the urging mechanism is configured for a stepwise dispensing of the substance contained in the cartridge body therefrom for effecting a portion-wise dispensing of a content of the cartridge body. This feature of the invention allows a simplified monitoring of the amount to be dispensed.

According to another aspect of the invention, the urging mechanism comprises a plurality of flexible portions adapted to engage one another for urging the cartridge actuator in the dispensing direction.

According to yet another aspect of the invention, each of the flexible portions includes teeth thereon adapted to engage the teeth of other flexible portions for urging the cartridge actuator in the dispensing direction. The teeth of the flexible portions may engage one another successively above the cartridge actuator upon actuation by the dispensing actuator.

According to a further aspect of the invention, the flexible portions are configured to engage one another to form a rigid longitudinal member above the cartridge actuator These flexible portions may be disposed between the dispensing device body and the cartridge body when the cartridge is received therein. Additionally, each of the flexible portions may change a direction of movement thereof upon actuation by the dispensing actuator at a transition region above the cartridge body for defining the first portion and the second portion.

According to yet a further aspect of the invention, the first portion moves in a direction opposite the second portion upon actuation of the urging mechanism by the dispensing actuator.

According to one aspect of the invention, the dispensing kit may further include a microprocessor coupled to the dispensing actuator for controlling an actuation thereof thereby effecting a controlled movement of the urging mechanism.

The invention advantageously allows the transfer of force in a linear direction by providing a multi-part urging mechanism which, when its different urging parts come together, allows force transfer, and where these different parts move in different directions with respect to the urging direction, thus affording a space saving alternative to urging mechanisms of the prior art. Such a solution is especially desirable for use in dispensers, such as dosing dispensers, apt to be transported.

Additionally, the dispensing cartridge according to the invention may be interchangeable with similar such dispensing cartridges when desired, such as when the content of the cartridge body has been fully dispensed. Thus, the actuating portion of the dispensing kit can be reused with refills, thereby providing a cost efficient alternative to non-refillable dispensers of the prior art.

Moreover, while, in dispensers of the prior art, the release of drops must be optically tracked and controlled in a careful manner in order to dispense the amount according to the prescription, the dispensing kit according to one aspect of the present invention advantageously allows a more accurate dispensing of drops from the cartridge.

BRIEF DESCRIPTION OF THE DRAWINGS

The invention will now be described in more detail, by way of example only, with reference to the accompanying drawings, in which like parts are identified by like reference numerals, and in which.

DETAILED DESCRIPTION OF THE INVENTION

Figure 1:
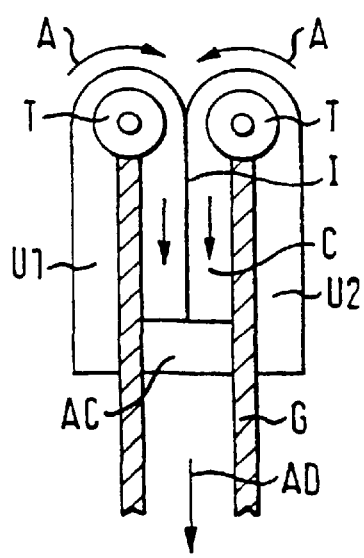
FIG. 1 is a partially cross sectional, partially cut away schematic view of an embodiment of an urging device according to the invention.

A schematic version of the principle of one embodiment of the urging device according to the invention is shown in FIG. 1, where the urging mechanism includes two flexible portions U1 and U2 which, when actuated in the direction of arrows A, move over transition mechanisms T and intermesh at an intermeshing region I for forming a consolidated longitudinal member C which pushes actuator AC in the actuating direction AD. This longitudinal member is guideable inside a guide housing G. It is to be noted that the intermeshing region I may be formed in any suitable manner, such as through friction of flexible portions U1 and U2, or through interlocking teeth, or any other conventional intermeshing mechanism as conventional in the art. Additionally, the urging mechanism may be actuated in the actuating direction AD either directly by transition mechanisms T, which, by any suitable conventional mechanism, may be turned in the direction of arrows A to intermesh flexible portions U1 and U2, or, in the alternative, this actuation may be effected by any other conventional means, such as a rod pushing flexible portions U1 and U2 in the actuating direction. The urging device shown in FIG. 1 advantageously allows the transfer of force through the use of a space saving urging mechanism having flexible portions which change direction during their actuation.

An alternative embodiment of the principle of the urging device according to the invention (not shown) may include a single flexible portion U1 changing its direction at a corresponding transition mechanism, such that no intermeshing is necessary. Additionally, the flexible portion or portions according to the invention need not change their direction during actuation by 180 degrees as shown in FIG. 1, but may simply move in two distinctly identifiable directions made possible by a corresponding transition mechanism or mechanisms. It is further to be noted that the transition mechanisms can take any suitable conventional form, such as rollers, for effecting the change in direction of the flexible portions.

The above principle for an urging device according to the invention may be implemented in a dispensing kit, which, according to the invention includes two separately identifiable (i.e. distinct) parts, one including a reservoir or cartridge having a reservoir or cartridge body, and the other including a dispensing device having a dispensing device body adapted to receive the cartridge body therein.

Figure 2:
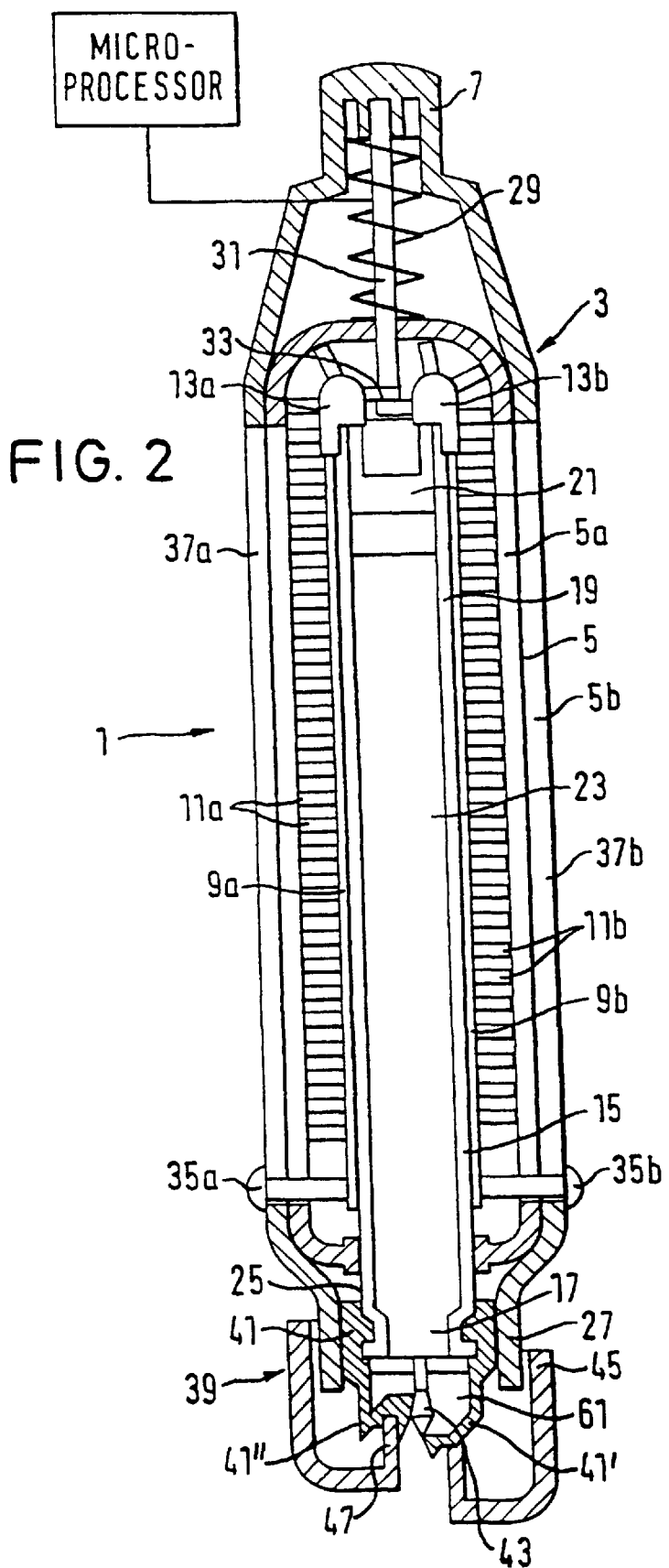
FIG. 2 is a longitudinal, cross sectional, view of one embodiment of the dispensing kit according to the invention where the urging device is in its initial position.

Referring now to FIG. 2, where one embodiment of the invention is shown, a dispensing kit 1 includes a dispensing device 3 having a dispensing device body or housing a dosing actuator 7, and an urging mechanism including on the one hand flexible portions 9a and 9b having teeth 11a and 11b thereon, and, on the other hand, transition mechanisms 13a and 13b. The dispensing kit according to the invention further includes a dispensing reservoir, which, according to the invention, is a cartridge adapted to be introduced into and taken out of the dispensing device body. The body of the cartridge, or cartridge body 15, defines an opening 17 at one end thereof, and a head portion 19 at another end thereof. The cartridge further includes a cartridge actuator 21, which, in the instant case, is a piston, disposed at head portion 19. The actuator 7 is preferably shaped as a button-like piece, comparable to similar such pieces formed on actuated pens and pencils Additionally, the dispensing device body can be provided with a clip (not shown) at the outside thereof, allowing the dispensing device and cartridge assembly to be conveniently available to the user, such as by being clipped to a pocket. The dispensing device and cartridge assembly may conveniently be shaped as a pen device for easy handling.

As further shown in FIG. 2, cartridge body 15 has a content 23 which, in the shown embodiment, is a liquid. However, as previously mentioned, the content may include any fluid or solid apt to be dispensed, such as tablets or capsules. In order to permit a slim shaping of the dispensing device, the cartridge is preferably sized for a content of up to 10 ml, preferably 3 ml. In FIG. 2, the cartridge body 15 is shown as having been introduced into the dispensing device body 5, its opening being in registration with an opening 25 disposed at a neck portion 27 of the dispensing device body 5.

In FIG. 2, the dispensing actuator 7 is further shown as comprising a button biased by a rod biasing member 29, which cooperates with a rod 31 for urging teeth is 11a and 11b forward, thus forming a rigid longitudinal member or rod 33 above cartridge actuator 21 of the cartridge. In the shown embodiment, the dispensing device body 5 is composed of an inner housing portion 5a which guides the flexible portions and fixes the cartridge body 15 after its insertion into the dispensing device body 5, and of an outer housing portion 5b, such a configuration imparting improved structural integrity to the dispensing device body.

The urging mechanism further includes restoring indicator knobs 35a and 35b fixed to chains 9a and 9b respectively, these knobs being effective for restoring the position of the chains from the final position shown in FIG. 3 (the description of which follows further below) to the starting position as shown in FIG. 2. Knobs 35a and 35b are guided in the dispensing device body in grooves 37a and 37b respectively, as better seen in FIG. 4.

The dispensing kit may comprise any suitable delivery mechanism 39 for allowing a dispensing of the content of the cartridge body 15 as is conventionally known in the art, such as drop-wise dispensing. Additionally, should the contents of the cartridge body be in the form of tablets or capsules, the delivery mechanism can take any suitable form for the individual dispensing of tablets or capsules as is conventionally known in the art, as will be explained in further detail below with respect to FIG. 7.

Figure 8:
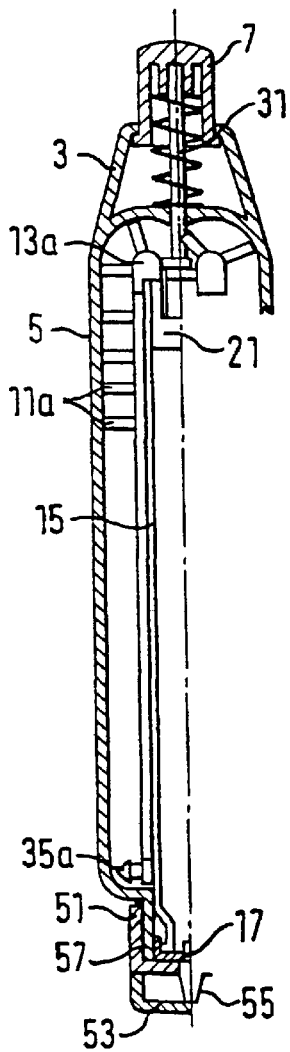
FIG. 8 is a view similar to FIG. 2 showing an alternative embodiment for the delivery mechanism of the dispensing kit.

The delivery mechanism 39 in the embodiment of FIG. 2 takes the form of a no-drip delivery mechanism including, as part of the cartridge, a flexible closure member 41 fitted onto the opening 17 of the cartridge body 15, and a guiding needle 43 attached to the cartridge body. The delivery mechanism 39 further includes a closure cap 45 having a flanged portion 47 for urging flexible closure member 41 onto the head of needle 43. In an alternative embodiment, as shown in FIG. 8, the delivery mechanism is brought into being by a perforation of a membrane 57 (which seals cartridge body 15 prior to its insertion into the dispensing device body) by a protrusion 55 on the flip-lid 53, as will be explained in further detail with respect to FIG. 8 below.

Figure 3:
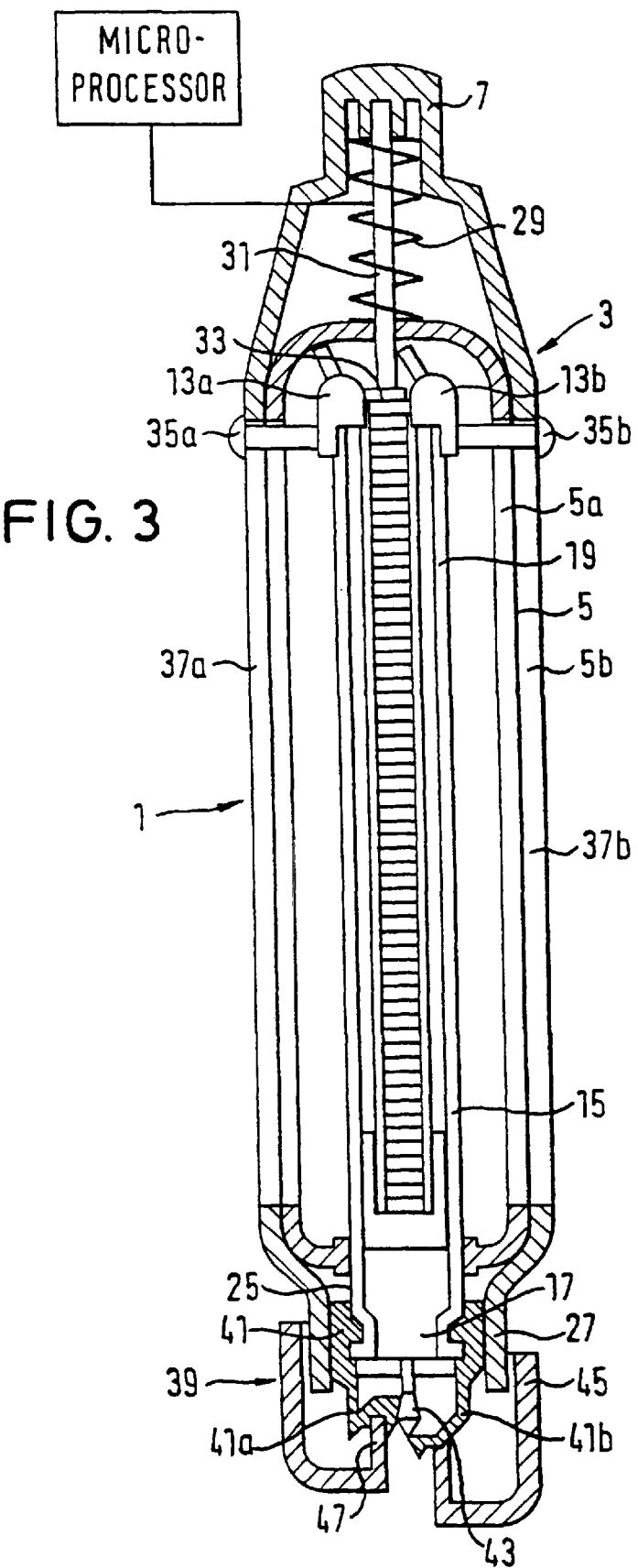
FIG. 3 is a view similar to FIG. 2, showing the urging device in its final position.

FIGS. 2 and 3 further show a microprocessor coupled to the dispensing actuator for controlling an actuation thereof thereby effecting a controlled movement of the urging mechanism. For example, in the shown dispensing kit, the microprocessor can be programmed to actuate the dispensing actuator a given set of times in order to dispense a prescribed or desired amount of the content 23 of cartridge body 15. Thus, the user of the dispensing kit can advantageously program the microprocessor according to his/her needs, the microprocessor being of a conventional type as within the knowledge of one skilled in the art.

FIG. 3 shows the dispensing kit of FIG. 2 with the urging device in its final position, that is, at a time when the dispensing device has effected a dispensing of the content 23 of cartridge body 15 to its maximum capacity. As seen in FIG. 3, in their final position, the flexible portions 9a and 9b have been moved by the dispensing actuator into an inner region of the cartridge body 15 forming the rigid member 33 thereon, knobs 35a and 35b further having moved to their topmost positions along grooves 37a and 37b.

Figure 4:
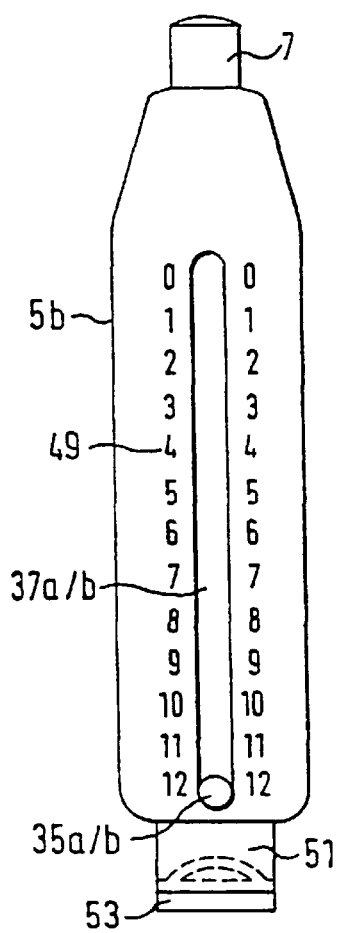
FIG. 4 is a front elevational view of the dispensing kit according to FIG. 2, further showing a closure lid.

As seen in FIG. 4, the outer housing body 5b may have a graduation 49 thereon corresponding to a dosing of liquid 23 from cartridge body 15 by way of the actuation of dispensing actuator 7. Further shown is one of the grooves 37a/b, and its corresponding knob 35a/b, which indicate in each instance the amount dispensed during actuation of dispensing actuator 7, and the total amount dispensed by virtue of graduation 49. FIG. 4 additionally shows an alternative closure cap 51 to the cap 45 shown in FIG. 2, this closure cap being openable and closeable by way of a flip-lid 53 as is conventional in the art.

Figure 5:
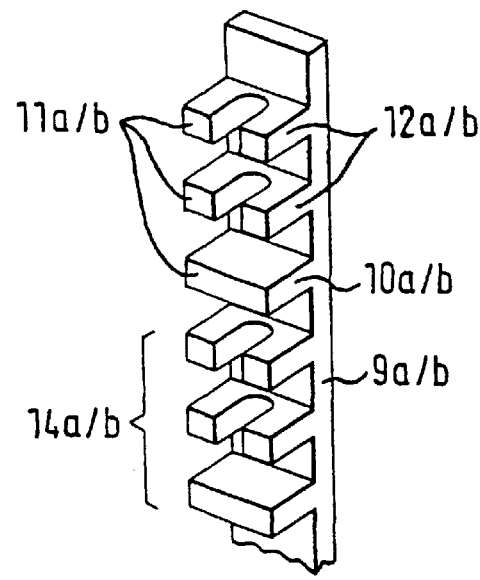
FIG. 5 is a partially cut away, perspective view of one embodiment of a flexible portion according to the invention.
Figure 6:
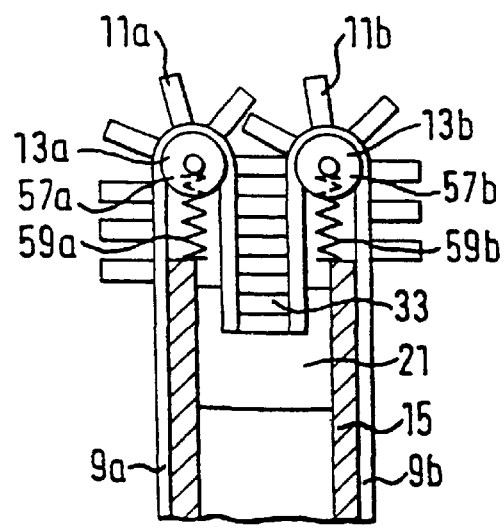
FIG. 6 is a cross-sectional view of a top portion of the cartridge body of FIG. 2 showing the transition mechanisms.

FIG. 5 shows a partially cut away perspective view of an embodiment of either of the flexible portions 9a/b. As is seen in FIG. 5, this embodiment includes flexible portion each including a set 14a/b of corresponding teeth 11a/b thereon, each set 14a/b including grooved teeth, 12a/b followed by a solid tooth 11a/b, the set 14a/b repeating itself along each flexible portion 9a/b for the length of the flexible portion As shown in FIG. 6, the urging mechanism according to the invention may include intermeshing teeth 11a and 11b of the two flexible portions 9a and 9b, such as teeth being ordered according to sets 14a/b shown in FIG. 5. One embodiment for the transition mechanisms is further shown in FIG. 6, according to which each transition mechanism includes a direction changing member 57a/b biased in a direction toward actuator 7 by biasing members 59a and 59b. The invention encompasses direction changing members and corresponding biasing members of any configuration as is conventional in the art for effecting a direction change of flexible portions 9a and 9b while further effecting a biasing of the direction changing members toward actuator 7.

Figure 7:
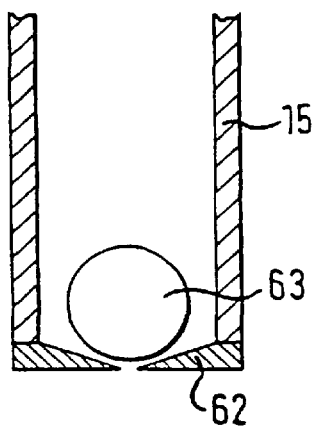
FIG. 7 is a cross-sectional, partially cut away view of a delivery mechanism in the dispensing kit according to the invention for dispensing solid tablets or capsules.

As seen in FIG. 7, an embodiment for a delivery mechanism 62 for the delivery of the content of cartridge body 15 in the form of tablets is shown. By way of example, the delivery mechanism may comprise a slitted flexible member 62, made from a material such as rubber or the like, which allows an expulsion of the tablet from the cartridge body through pressure received thereon by an actuation of the urging device according to the invention, and which thereafter reassumes its original closed shape by virtue of material memory.

As shown in FIG. 8, the closure cap 51 may advantageously be formed in one embodiment of the invention as a cap having a needle-like protrusion 55 at an inner central region thereof. In this embodiment, the cartridge is sealed by a membrane 57 before its insertion into the dispensing device body. After insertion of the cartridge therein, the closure cap is placed onto the opening of the dispensing device body, the protrusion 55 thereby extending into a region of the opening of the dispenser device body and perforating the closure membrane 57 of the cartridge. After this step, the dispensing device and cartridge assembly are ready for dispensing the content of the cartridge from the opening created by a perforation of membrane 57 by protrusion 55.

The cartridge body 15 may be inserted into the dispensing device in any suitable way. According to one aspect, the dispensing device body 5 may be made of two or more parts which may be disassembled in a suitable way for allowing an introduction of the cartridge body 15 therebetween before the parts are fastened back together. According to another aspect, the closure cap 45 in the embodiment of FIGS. 2 and 3, or closure cap 51 in the embodiment of FIGS. 4 and 8, may be removed, allowing the introduction of the cartridge body 15 into the dispensing device body 5. Thereafter, the closure caps may be repositioned on to the dispensing device body 5 as shown in the figures.

The operation of the urging device and dispensing device implementing the same according to the invention is set forth below.

Referring to FIGS. 2, 3 and 4 according to the invention, whenever a content of a cartridge body 15 is to be dispensed, the cartridge is introduced into the dispensing device body 5 when the urging device is in its initial position as shown in FIG. 2, its opening 17 being placed in registration with the opening in the dispensing device body 5 Should the flexible portions 9a/b have been displaced from their initial positions, as indicated by a lowest position of restoring knobs 35a and 35b, these knobs can be pulled down manually. With the dispensing kit so assembled, a delivery of the content 23 of cartridge body 15 may be effected by pushing downward on actuator 7, which in turn presses down upon the teeth 11a or 11b of flexible portions 9a or 9b, depending on which tooth is exposed to rod 31 of actuator 7. The pushing down of rod 31 therefore forces the teeth to intermesh with one another above cartridge actuator 21, in the form of a rigid longitudinal member or rigid member 33. Rigid member 33 then pushes actuator 21 downward, thus effecting a dispensing of the content of cartridge body 15 therefrom. The rod is thereafter biased upward by rod biasing member 29 into its initial, non-actuated position. Referring now to FIGS. 5 and 6, it can be appreciated that, for the embodiment of the flexible portions 9a/b shown in those figures, rod 31 will be pushing on a solid tooth 10a/b, pushing it downward, and emerging from the intermeshing region of the flexible portions 9a/b through the grooves of grooved teeth 12a/b to its initial position, having thus intermeshed the teeth 11a/b in a first intermeshing stage. In order to present a further solid tooth to the rod 31 for the next dispensing actuation, the teeth go through a secondary intermeshing stage through the action of transition mechanisms 13a/b, as shown in FIG. 6. It can be appreciated from FIG. 6 that a pushing down of the teeth 11a/b in the first intermeshing stage by rod 31 biases biasing members 59a and 59b downward, and that a restoring of the rod 31 to its initial position by way of rod biasing member 29 releases the biasing members 59a and 59b from a state of compression. The release of biasing members 59a and 59b causes a movement of the flexible positions in the intermeshing direction for a further intermeshing of teeth 11a and 11b in a second intermeshing stage, which ensures that a subsequent actuation of rod 31 will result in rod 31 acting on the next available solid tooth 10a/b of the intermeshing flexible portions 9a/b.

As can be appreciated from the shown figures, the invention permits a simple, space saving alternative to force transfer mechanisms of the prior art. It should be noted that, although in the shown embodiments in FIGS. 2 to 6, the urging device is configured for a step-wise delivery of the content of cartridge body 15, it would also be possible according to the invention to have a continuous dispensing mechanism, as for example suggested in the schematic depiction of the urging device according to the invention shown in FIG. 1. In the embodiment of FIGS. 2 to 6, the distances between given sets of teeth correspond to the actuation distance of the dispensing device for each push of dispensing actuator 7

The no-drip delivery mechanism shown in FIGS. 2 and 3 functions as follows. To allow a delivery of the content 23 of cartridge body 15, the actuator 7 is initially actuated as previously described, resulting in a delivery of the liquid content of cartridge body 15 onto delivery chamber 61 formed by the walls of the flexible closure member 41. The volume of delivery chamber 61 would therefore correspond to one dose of the content of the cartridge body. Thereafter, closure cap 45 is pressed onto flexible closure member 41 for urging this member 41 at least partially past the head of needle 43, and for thus changing the wall configuration of chamber 61 from configuration 41' to configuration 41" as shown, and for reducing a volume of chamber 61, thus effecting a delivery of liquid from the chamber. Upon a release of closure cap 45, the volume of chamber 61 goes back to its initial size, creating a vacuum in the chamber, and thus tending to suck back any liquid remaining on or about the needle, in this way preventing drips from the dispensing device after delivery. As stated previously, however, the above no-drip delivery mechanism is but one form for the delivery mechanism adapted to be used as part of the dispensing kit according to the invention, and may take any suitable conventional form, as an alternative to the inventive embodiment described above.

It will be understood that the embodiment described above is in no way limiting and lends itself to any desirable modification, without departing from the scope of the invention, as set forth in the appended claims.

What is claimed is:

1. An urging device comprising:
   an urging actuator; and
   an urging mechanism disposed to be actuatable by the urging actuator in an urging direction for effecting a translational movement of a member to be moved in the urging direction,
   the urging mechanism being configured such that, upon actuation thereof by the urging actuator, at least a first portion thereof moves in a first direction, and a second portion thereof moves in a second direction substantially opposite to the first direction,
   and said member adopted to be moved in the urging direction upon engagement with at least two flexible portions,
   wherein the urging mechanism comprises one of said flexible portions forming the first portion and the second portion, the urging device further including a transition mechanism coupled to the flexible portion for guiding a direction change of the flexible portion form the first direction to the second direction upon actuation of the urging mechanism, and
   wherein the flexible portion is a first flexible portion and the transition mechanism is a first transition mechanism, the urging mechanism further comprising a second flexible portion and a second transition mechanism coupled to the second flexible portion for guiding a direction change of the flexible portion from the first direction to the second direction, the first flexible portion and the second flexible portion being adapted to engage one another at an engaging zone after having been guided by the first transition mechanism and the second transition mechanism thereby forming a consolidated longitudinal member corresponding to the second portion of each of the first flexible portion and the second flexible portion, the consolidated longitudinal member being effective for effecting the translational movement of the member to be moved in the urging direction, and wherein:
   the second direction differs from the first direction by an angle of 180 degrees, and
   the urging device further includes a first biased member connected to the first transition mechanism and a second biased member connected to the second transition mechanism, the first biased member and the second biased member being respectively effective for biasing the first transition mechanism and the second transition mechanism in the first direction, such that, upon an actuation of the urging actuator, the first biasing member and the second biasing member are compressed for respectively allowing the first transition mechanism and the second transition mechanism to move in the second direction, and that, upon a release of the urging actuator, the first transition mechanism and the second transition mechanism move in the first direction thereby effecting an engagement of the first flexible portion and the second flexible portion with one another without actuation by the urging actuator.

2. The urging device according to claim 1, wherein the transition mechanism is the urging actuator.

3. The urging device according to claim 1, wherein the first flexible portion and second flexible portion are configured to engage one another at the engaging zone by friction.

4. The urging device according to claim 1, wherein each of the first flexible portion and second flexible portion has teeth disposed thereon which respectively engage one another at the engaging zone for forming a rigid longitudinal member corresponding to the consolidated longitudinal member.

5. The urging device according to claim 1, wherein the urging actuator comprises a rod biased in a direction opposite the urging direction, and wherein each of the first flexible portion and the second flexible portion further has teeth thereon, said teeth comprising repeated sets of shaped teeth, each set including a plurality of grooved teeth and a solid tooth such that, upon actuation of the urging actuator, the rod presses upon the solid tooth of a nearest flexible portion for intermeshing the teeth with one another in the urging direction, and further such that, upon release of the urging actuator, the rod is biased in a direction opposite the urging direction through the grooved teeth, the biased members connected to the transition mechanisms thereafter being effective for causing a further intermeshing of the teeth for further engagement of a solid tooth by the rod.

6. The urging device according to claim 1, further including a microprocessor operatively coupled to the urging actuator for controlling an actuation thereof thereby effecting a controlled movement of the member to be moved in the urging direction.

7. A dispensing kit comprising:
a dispensing cartridge including:
a cartridge body defining an, opening at one end thereof and a head portion at another end thereof and
a cartridge actuator being disposed at said head portion; and a dispensing device having:
a dispensing device body for receiving said cartridge body therein and defining an opening at one end thereof such that, when said cartridge body is within the dispensing device body, the opening of the dispensing device body is in registration with the opening of the cartridge body;
a dispensing actuator disposed at another end of the dispensing device body; and
an urging mechanism disposed in the dispensing device body for being actuatable by the dispensing actuator to urge the cartridge actuator in a dispensing direction when the cartridge body is received within the dispensing device for effecting a dispensing of a content of the cartridge body therefrom, the urging mechanism being configured such that, upon actuation thereof by the dispensing actuator, at least a first portion thereof moves in a first direction and a second portion thereof moves in a second direction substantially opposite to the first direction,
wherein the cartridge actuator is formed by an engagement of at least two flexible portions.

8. The dispensing kit according to claim 7, wherein the urging mechanism is configured for a stepwise dispensing of the content of the cartridge body therefrom for effecting a portion-wise dispensing of the content of the cartridge body.

9. The dispensing kit according to claim 7, wherein the urging mechanism comprises a plurality of flexible portions adapted to engage one another for urging the cartridge actuator in the dispensing direction.

10. The dispensing kit according to claim 9, wherein each of the flexible portions includes teeth thereon adapted to engage the teeth of other flexible portions for urging the cartridge actuator in the dispensing direction.

11. The dispensing kit according to claim 10, wherein the teeth of the flexible portions engage one another successively above the cartridge actuator upon actuation by the dispensing actuator.

12. The dispensing kit according to claim 9, wherein the flexible portions are configured to engage one another to form a rigid longitudinal member above the cartridge actuator.

13. The dispensing kit according to claim 9, wherein each of the flexible portions changes a direction of movement thereof upon actuation by the dispensing actuator at a transition region above the cartridge body for defining the first portion and the second portion.

14. The dispensing kit according to claim 7, wherein the first portion moves in a direction opposite the second portion upon actuation of the urging mechanism by the dispensing actuator.

15. The dispensing kit according to claim 7, further including a microprocessor operatively coupled to the dispensing actuator for controlling an actuation thereof thereby effecting a controlled movement of the urging mechanism.

16. A dispensing kit according to claim 7, further comprising a material disposed in the cartridge body, the material comprising the content of the cartridge body, and wherein the material comprises one of a fluid and a plurality of solid parts.

17. The combination according to claim 16, wherein the material includes one of pharmaceuticals, foodstuff and cosmetics.

* * * * *

UNITED STATES PATENT AND TRADEMARK OFFICE
CERTIFICATE OF CORRECTION

PATENT NO. : 6,488,183 B1
DATED : December 3, 2002
INVENTOR(S) : Braeuninger-Weimer et al.

It is certified that error appears in the above-identified patent and that said Letters Patent is hereby corrected as shown below:

<u>Title page,</u>
Item [73], delete "GmnH" and substitute with -- GmbH --;

Signed and Sealed this

Eleventh Day of March, 2003

JAMES E. ROGAN
*Director of the United States Patent and Trademark Office*